United States Patent
Scott

(10) Patent No.: US 10,799,687 B1
(45) Date of Patent: Oct. 13, 2020

(54) URINARY CATHETER INSERTION ALIGNMENT DEVICE FOR A FEMALE PATIENT, METHOD FOR MAKING SAME, AND METHOD FOR USING SAME

(71) Applicant: David O. Scott, Morristown, IN (US)

(72) Inventor: David O. Scott, Morristown, IN (US)

( * ) Notice: Subject to any disclaimer, the term of this patent is extended or adjusted under 35 U.S.C. 154(b) by 0 days.

(21) Appl. No.: 16/723,602

(22) Filed: Dec. 20, 2019

(51) Int. Cl.
*A61M 25/00* (2006.01)
*A61M 25/09* (2006.01)
*A61B 17/02* (2006.01)

(52) U.S. Cl.
CPC ....... *A61M 25/09041* (2013.01); *A61B 17/02* (2013.01); *A61M 25/0017* (2013.01); *A61M 2025/09133* (2013.01); *A61M 2210/1092* (2013.01); *A61M 2210/1475* (2013.01)

(58) Field of Classification Search
None
See application file for complete search history.

*Primary Examiner* — Monica A Huson
*Assistant Examiner* — Kelsey C Grace
(74) *Attorney, Agent, or Firm* — Ice Miller LLP

(57) ABSTRACT

A urinary catheter insertion alignment device for use by a female patient is disclosed. The urinary catheter insertion alignment device is molded to the patient's vaginal anatomy using impression material while an intermittent urinary catheter is inserted into the urethral orifice. Once the urinary catheter insertion alignment device has hardened, the intermittent urinary catheter is removed therefrom. Thereafter, the urinary catheter insertion alignment device may be fitted to the vaginal anatomy by the patient, which positions the passageway therethrough (formerly occupied by the urinary catheter in place during the molding operation) directly over the urethral orifice. The patient may then easily insert an intermittent urinary catheter (of a size smaller than that used during the molding operation) through the passageway, into the urethral orifice, and into the bladder for drainage of the bladder.

19 Claims, 3 Drawing Sheets

US 10,799,687 B1

URINARY CATHETER INSERTION ALIGNMENT DEVICE FOR A FEMALE PATIENT, METHOD FOR MAKING SAME, AND METHOD FOR USING SAME

TECHNICAL FIELD OF THE DISCLOSED EMBODIMENTS

The embodiments disclosed herein generally relate to urinary catheters and, more specifically, to a urinary catheter insertion alignment device and method.

BACKGROUND OF THE DISCLOSED EMBODIMENTS

A urinary catheter is a flexible tube for draining urine from the bladder. It may be necessary for a person to use a urinary catheter if they have difficulty passing urine naturally. Reasons for needing a catheter can include: a blockage in the urethra, which is the passageway that carries urine out of the bladder; injury to the urethra; birth defects affecting the urinary tract; kidney, ureter, or bladder stones; bladder weakness or nerve damage; or tumors within the urinary tract or reproductive organs, to name just a few reasons.

An intermittent catheter, also known as a standard catheter, is a thin, flexible tube that a person temporarily inserts into their bladder through the urethra. The external end of the tube may be left open, allowing the urine to drain into a receptacle. Another option is to attach the tube to an external drainage bag, which collects the urine. Once the bladder has been emptied, the catheter needs to be removed. It is necessary to remove the old catheter and insert a new one several times per day to empty the bladder.

For patients who cannot insert an intermittent catheter through their urethra, it is necessary to install a suprapubic catheter. A suprapubic catheter is surgically inserted approximately two inches below the navel directly into the bladder, just above the pubic bone. This allows urine to be drained without having to insert a catheter into the urethra.

Most patients would prefer to avoid such a surgical procedure, but many female patients find it difficult, if not impossible, to insert a urinary catheter into their urethra daily, or several times a day, for a variety of reasons. A reason stated by many patients is simply the physically difficult task of locating their urethral orifice and inserting the end of a very small diameter tube therein.

There is therefore a need for a device that will assist a female patient in locating the urethral orifice and inserting an intermittent urinary catheter therein. The presently disclosed embodiments are directed toward meeting this need.

SUMMARY OF THE DISCLOSED EMBODIMENTS

In one embodiment, a method of forming a urinary catheter insertion alignment device for a female patient is disclosed, the method comprising the steps of: a. spreading the labia majora and labia minora of the patient to expose a urethral orifice of the patient; b. inserting an intermittent urinary catheter into the urethral orifice of the patient; c. applying impression material to an area surrounding the catheterized urethral orifice; d. allowing the impression material to harden; e. removing the hardened impression material and the urinary catheter from the patient; and f. removing the urinary catheter from the hardened impression material to form the urinary catheter insertion alignment device.

In one embodiment, a urinary catheter insertion alignment device formed from the above method is disclosed.

In one embodiment, a method for using a urinary catheter insertion alignment device for insertion of an intermittent urinary catheter into the urethral orifice of a female patient is disclosed, the method comprising the steps of: a. spreading the labia majora and labia minora of the patient to expose a urethral orifice of the patient; b. placing a urinary catheter insertion alignment device, which is shaped to conform to the patient's vaginal anatomy, over the urethral orifice, thereby aligning a passageway formed through the urinary catheter insertion alignment device is positioned over the urethral orifice; and c. inserting an intermittent urinary catheter through the passageway and into the aligned urethral orifice until a distal end of the intermittent urinary catheter is positioned inside the patient's bladder.

Other embodiments are also disclosed.

BRIEF DESCRIPTION OF DRAWINGS

The present invention will become more fully understood from the detailed description and the accompanying drawings, wherein.

DETAILED DESCRIPTION OF THE DISCLOSED EMBODIMENTS

Figure 1:
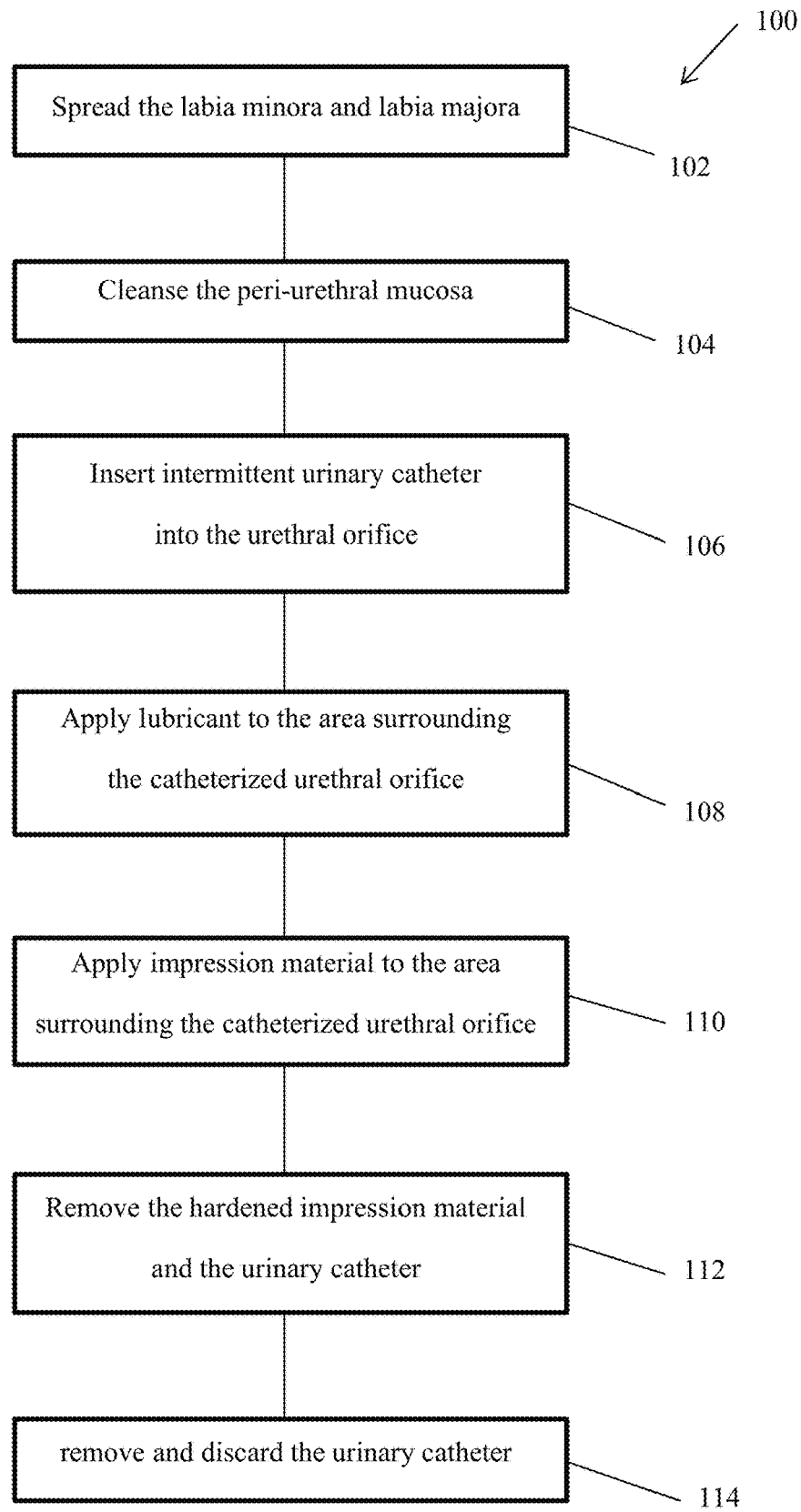
FIG. 1 is a schematic process flow diagram for making an intermittent urinary catheter insertion alignment device in accordance with an embodiment.

For the purposes of promoting an understanding of the principles of the invention, reference will now be made to the embodiments illustrated in the drawings, and specific language will be used to describe those embodiments. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated and desired to be protected. Such alternative embodiments require certain adaptations to the embodiments discussed herein that would be obvious to those skilled in the art.

FIG. 1 is a schematic flow diagram illustrating one embodiment of a method for making a urinary catheter insertion alignment device that is customized for the vaginal anatomy of a particular female patient. The process is indicated generally at 100. The process 100 will normally be performed by one to two medical or technical operators, and preferably within a sterile field. The first step 102 in the process 100 is to place a finger to the left and to the right of the urethral orifice at the vestibular level and spread the labia minora and labia majora until the external urethral orifice is exposed and standing alone. Alternatively, the labia may be spread with the help of a retractor instrument. Step 102 may be performed by an assistant to the operator performing the remaining steps of the process 100, or may be performed by a sole operator using the non-dominant hand.

At step 104, the peri-urethral mucosa is cleansed with cleansing solution. The peri-urethral mucosa is cleansed anterior to posterior, inner to outer, one swipe per swab, with the swab being discarded away from the sterile field. In some embodiments, the swab is grasped with forceps during the cleansing process.

At step 106, the operator picks up an intermittent urinary catheter, such as a 16 Fr/Ch (5.3 mm) intermittent urinary catheter, to name just one non-limiting embodiment, and inserts the catheter into the urethral orifice to a depth of approximately 20 mm. The intermittent urinary catheter used at step 106 should be slightly larger than the intermittent urinary catheter that is desired to be inserted into the patient at later times.

At step 108, while the labia remain spread, the operator applies a small amount of sterile lubricant, such as a sterile oil lubricant, to the area surrounding the catheterized urethral orifice and onto approximately the first 40-50 mm of the intermittent urinary catheter protruding from the urethral orifice.

At step 110, an impression material is applied to the area around the catheterized urethral orifice to a depth of approximately 20 mm in an embodiment. The impression material is applied to the area approximately 30 mm on either side of the urethral orifice in an embodiment. The impression material may continue to be applied down the length of the vagina and the perineum, but not to the anus, in an embodiment. In one embodiment, the impression material comprises super hydrophilic vinyl polysiloxane. Super hydrophilic vinyl polysiloxane is commonly used to make dental impressions and is approved by the U.S. Food and Drug Administration (FDA). It will "set up" (harden) in approximately one minute. In other embodiments, any biocompatible molding material may be used.

In some embodiments, a concave mold may be applied to the impression material after it is applied to the patient in order to create a desired exterior surface contour. In other embodiments, the concave mold is applied around the catheterized urethra prior to applying the impression material, and the impression material is injected into the interior of the mold.

At step 112, the hardened impression material, along with the catheter, are removed from the patient. At step 114, the catheter is extracted from the impression material and discarded. It will be appreciated that the hardened impression material will retain the shape of the patient's vaginal anatomy, and therefore may function as a urinary catheter insertion alignment device for future insertions of urinary catheters.

Figure 3:
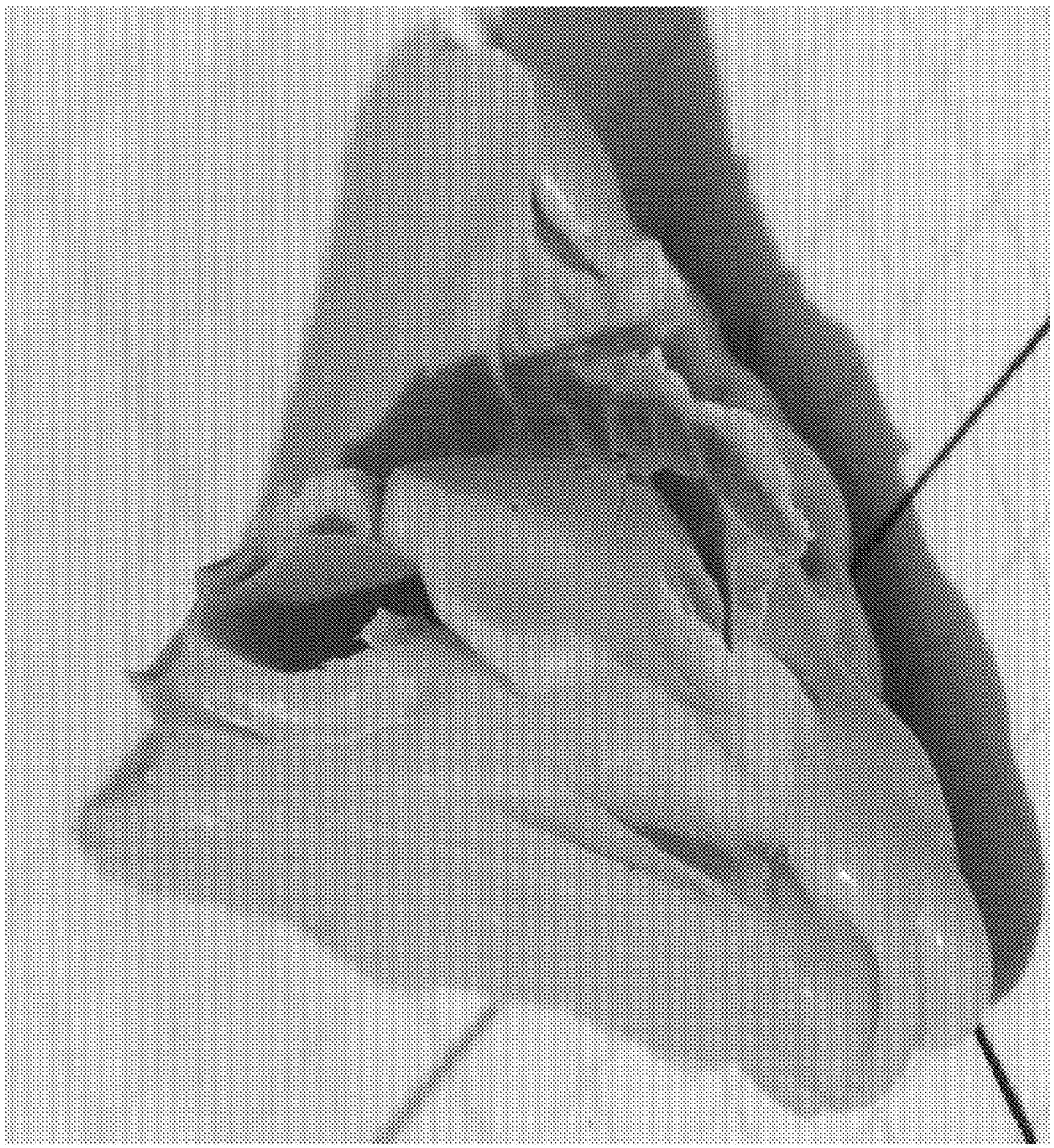
FIG. 3 is an example of an intermittent urinary catheter insertion alignment device in accordance with an embodiment.

FIG. 3 illustrates an example of an intermittent urinary catheter insertion alignment device formed in accordance with the method of FIG. 1.

Figure 2:
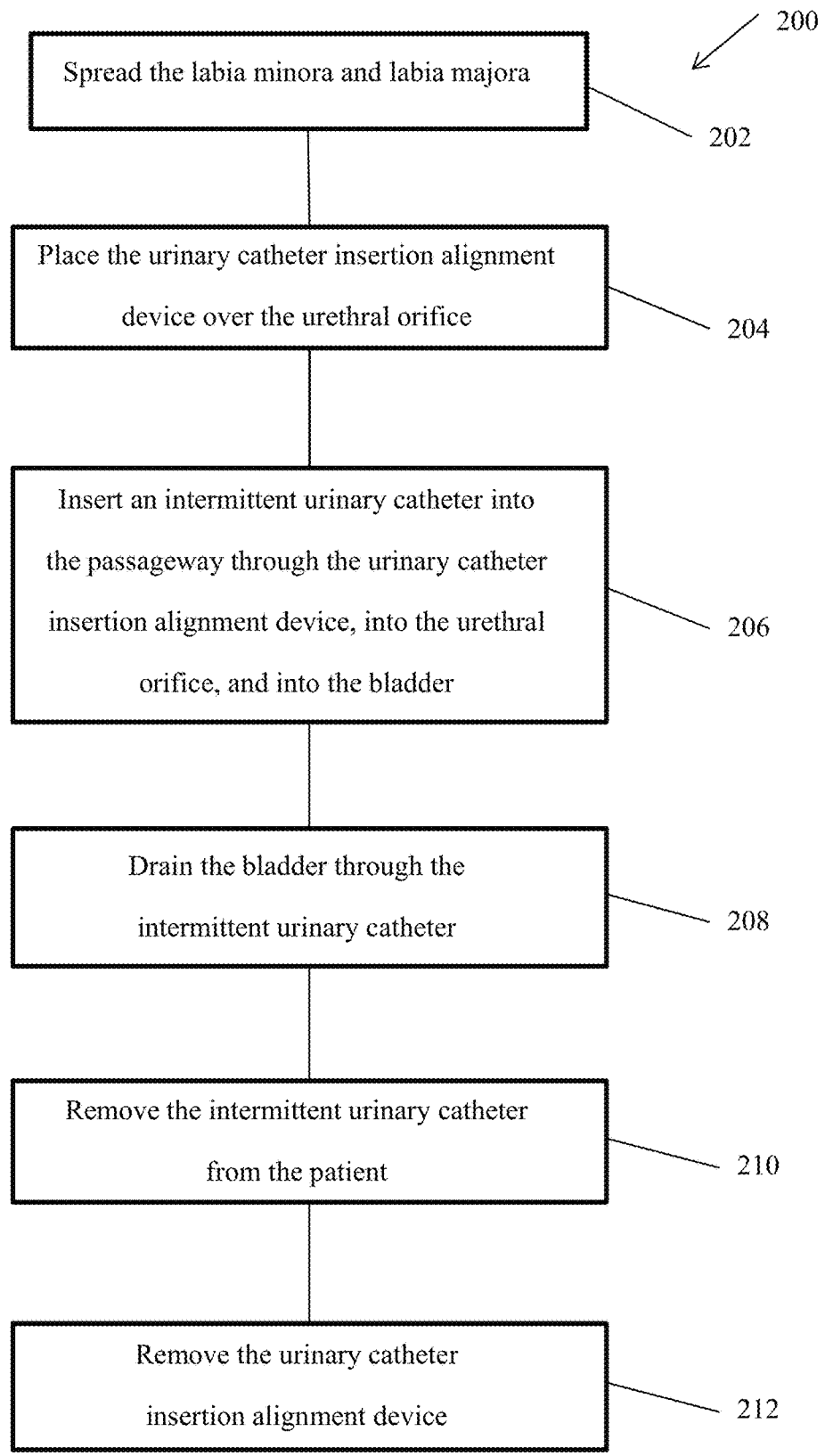
FIG. 2 is a schematic flow diagram illustrating one embodiment of a method for using a urinary catheter insertion alignment device to insert an intermittent urinary catheter into a female patient in accordance with an embodiment.

FIG. 2 is a schematic flow diagram illustrating one embodiment of a method for using a urinary catheter insertion alignment device to insert an intermittent urinary catheter into a female patient. The process illustrated in FIG. 2 is indicated generally at 200. The process 200 may be performed by the patient when she desires to insert an intermittent urinary catheter. At step 202, the patient places a finger to the left and to the right of the urethral orifice at the vestibular level and spreads the labia minora and labia majora until the external urethral orifice is exposed and standing alone.

At step 204, the patient places the urinary catheter insertion alignment device over the urethral orifice. Since the urinary catheter insertion alignment device was molded to conform to the patient's vaginal anatomy, it is keyed thereto and is easily positioned such that the passageway therethrough (that formerly contained the 16 Fr/Ch (5.3 mm) intermittent urinary catheter during the process of forming the urinary catheter insertion alignment device) is positioned directly over the urethral orifice.

At step 206, the patient selects an intermittent urinary catheter of a size smaller than the intermittent urinary catheter used during the process of forming the urinary catheter insertion alignment device. For example, the patient may select a 14 Fr/Ch (4.7 mm) intermittent urinary catheter, which will easily pass through the 16 Fr/Ch (5.3 mm) passageway through the urinary catheter insertion alignment device. The intermittent urinary catheter may be lubricated prior to insertion. The patient inserts the intermittent urinary catheter into the passageway through the urinary catheter insertion alignment device, and the passageway guides the intermittent urinary catheter directly to the urethral orifice, such that further insertion of the intermittent urinary catheter will cause the distal end of the catheter to enter the urethral orifice and will ultimately place the distal end thereof inside the patient's bladder.

At step 208, the bladder is drained through the intermittent urinary catheter. At step 210, the patient removes the intermittent urinary catheter after the bladder has been drained. At step 212, the patient removes the urinary catheter insertion alignment device from the vagina.

It will be appreciated from the foregoing that the urinary catheter insertion alignment device described in the various embodiments hereinabove allows for precise positioning of the distal end of an intermittent urinary catheter at the urethral orifice due to the keying of the urinary catheter insertion alignment device's shape to the patient's vaginal anatomy. Use of the urinary catheter insertion alignment device therefore allows the patient to easily insert the intermittent urinary catheter into the bladder for drainage thereof.

While the detailed description elaborates workable embodiments of the present invention, the embodiments shall not be construed as a limitation on the patented scope and claims of the present invention and, furthermore, all equivalent adaptations and modifications based on the technological spirit of the present invention shall remain protected within the scope and claims of the invention herein.

What is claimed is:

1. A method of forming a urinary catheter insertion alignment device for a female patient, the method comprising the steps of:
   a. spreading the labia majora and labia minora of the patient to expose a urethral orifice of the patient;
   b. inserting an intermittent urinary catheter into the urethral orifice of the patient;
   c. applying impression material to an area surrounding the catheterized urethral orifice;
   d. allowing the impression material to harden;
   e. removing the hardened impression material and the urinary catheter from the patient; and
   f. removing the urinary catheter from the hardened impression material to form the urinary catheter insertion alignment device.

2. The method of claim 1, wherein at least steps (a)-(e) are performed within a sterile field.

3. The method of claim 1, wherein step (a) further comprises placing a finger of an operator to the left and to the right of the urethral orifice at the vestibular level and spreading the labia majora and labia minora until the external urethral orifice is exposed and standing alone.

4. The method of claim 1, wherein step (a) further comprises spreading the labia majora and labia minora using a retractor instrument.

5. The method of claim 1, further comprising the step of: after step (a) and before step (b), cleansing the peri-urethral mucosa of the patient with a cleansing solution.

6. The method of claim 1, wherein the intermittent urinary catheter comprises a 16 Fr/Ch (5.3 mm) intermittent urinary catheter.

7. The method of claim 1, wherein step (b) comprises inserting the intermittent urinary catheter into the urethral orifice of the patient to a depth of approximately 20 mm.

8. The method of claim 1, further comprising the step of: after step (b) and before step (c), applying a quantity of sterile lubricant to an area surrounding the catheterized urinary orifice and onto approximately the first 40 mm of the intermittent urinary catheter protruding from the urinary orifice.

9. The method of claim 1, wherein step (c) further comprises applying the impression material to the area surrounding the catheterized urethral orifice approximately 30 mm on either side of the urethral orifice and to a depth of approximately 20 mm.

10. The method of claim 1, wherein step (c) further comprises applying the impression material to the area surrounding the catheterized urethral orifice and down the length of the vagina and the perineum, but not to include the anus.

11. The method of claim 1, wherein the impression material comprises super hydrophilic vinyl polysiloxane.

12. The method of claim 1, further comprising the step of: after step (c) and before step (d), molding a desired surface contour onto an exterior surface of the impression material.

13. The method of claim 1, further comprising the step of: prior to step (c), positioning a concave mold around the catheterized urethral orifice, wherein step (c) comprises injecting the impression material into an interior of the mold.

14. A method for using a urinary catheter insertion alignment device for insertion of an intermittent urinary catheter into the urethral orifice of a female patient, the method comprising the steps of:

a. spreading the labia majora and labia minora of the patient to expose a urethral orifice of the patient;

b. placing a urinary catheter insertion alignment device, which is shaped to conform to the patient's vaginal anatomy, over the urethral orifice, thereby aligning a passageway formed through the urinary catheter insertion alignment device is positioned over the urethral orifice; and c. inserting an intermittent urinary catheter through the passageway and into the aligned urethral orifice until a distal end of the intermittent urinary catheter is positioned inside the patient's bladder.

15. The method of claim 14, further comprising the step of:

d. draining the bladder through the intermittent urinary catheter.

16. The method of claim 15, further comprising the steps of:

e. removing the intermittent urinary catheter from the bladder and from the passageway of the urinary catheter insertion alignment device; and f. removing the urinary catheter insertion alignment device from the patient.

17. The method of claim 1, wherein step (a) further comprises placing a finger of the patient to the left and to the right of the urethral orifice at the vestibular level and spreading the labia majora and labia minora until the external urethral orifice is exposed and standing alone.

18. The method of claim 14, wherein the intermittent urinary catheter comprises a 14 Fr/Ch (4.7 mm) intermittent urinary catheter and the passageway comprises a 16 Fr/Ch (5.3 mm) diameter.

19. A urinary catheter insertion alignment device formed by the process of claim 1.

\* \* \* \* \*